United States Patent [19]

Shepard

[11] Patent Number: 4,738,665
[45] Date of Patent: Apr. 19, 1988

[54] METHOD AND APPARATUS FOR CONTROLLING FLOW RATE OF FLUID

[75] Inventor: Michael H. Shepard, Cockeysville, Md.

[73] Assignee: Hall Hill Co., Houston, Tex.

[21] Appl. No.: 781,010

[22] Filed: Sep. 27, 1985

[51] Int. Cl.⁴ .............................................. A61M 5/00
[52] U.S. Cl. ....................................... 604/248; 137/1; 138/43
[58] Field of Search ................. 138/43, 42, 46; 137/1; 251/126; 604/248, 246

[56] References Cited

U.S. PATENT DOCUMENTS

| | | |
|---|---|---|
| 1,964,300 | 6/1934 | Perry et al. |
| 2,236,084 | 3/1941 | Brown |
| 2,323,115 | 6/1943 | Bryant .................................. 138/43 |
| 2,833,311 | 5/1958 | Baldelli |
| 3,532,126 | 10/1970 | Boothe |
| 3,532,127 | 10/1970 | Vogelsang et al. |
| 4,011,893 | 3/1977 | Bentley .................................. 138/43 |
| 4,275,767 | 6/1981 | Westfall |
| 4,552,178 | 11/1985 | Olsson |
| 4,634,434 | 1/1987 | Marino .................................. 604/246 |

Primary Examiner—Alan Cohan
Attorney, Agent, or Firm—Antonelli, Terry & Wands

[57] ABSTRACT

A method and an apparatus for controlling the flow rate of a fluid are disclosed. Fluid is flowed through an elongated passage having a small cross-sectional area to control the flow rate thereof. The length of the elongated passage through which the fluid is flowed is changed in a predetermined manner to change the flow rate of fluid. The apparatus comprises a first member having a spiral shaped elongated groove with a small cross-sectional area formed in a surface thereof and a second member having a surface overlying the groove to form the elongated passage for controlling the flow rate of the fluid. A second groove having a substantially larger cross-sectional area than the elongated passage is formed in the surface of the second member and configured such that it can be selectively placed in communication with spaced locations of said first groove thereby effectively bypassing a portion of the elongated passage and changing the length of the elongated passage through which the fluid is flowed whereby the flow rate of fluid flowed through the elongated passage is changed. The relative position of the first and second members is changed to adjust the length of the elongated passage which is bypassed.

14 Claims, 3 Drawing Sheets

METHOD AND APPARATUS FOR CONTROLLING FLOW RATE OF FLUID

BACKGROUND AND SUMMARY OF THE INVENTION

The present invention is directed to a method and apparatus for controlling the flow rate of a fluid. The method and apparatus involve flowing a fluid through an elongated passage having a small cross-sectional area which limits the flow rate of the fluid. The flow rate is adjusted by changing the length of the elongated passage through which the fluid is flowed. The method and apparatus of the invention may be used, for example, for intravenous infusion of liquid solutions, for controlling the flow of gases in gas chromatography, for metering drugs into diluents, dies into foodstuffs, etc.

The flow of a fluid from an enclosed pressure vessel can be controlled by passing the fluid through a passage having a small cross-sectional area and a considerable length. The theoretical flow rate through a tube having a cylindrical cross-section, for example, can be calculated from the following equation:

$$F = \frac{\pi r^2}{8 \mu L} \times dp$$

where:
F=Flow rate
r=Bore radius
$\mu$=Fluid viscosity
L=Passage length
dp=Pressure difference.

The method and apparatus of the present invention takes advantage of this relationship to effect a change in the controlled flow rate of a fluid through an elongated passage having a small cross-sectional area by changing the length of the elongated passage through which the fluid is flowed. More particularly, the method of the invention for controlling the flow rate of a fluid comprises the steps of providing an elongated passage having a small cross-sectional area, supplying fluid to the elongated passage to flow the fluid through a first predetermined length of the elongated passage at a first flow rate, and changing the flow rate of fluid in the passage from the first flow rate to a second flow rate by changing the length of the elongated passage through which the fluid is flowed from the first predetermined length to a second predetermined length.

The elongated passage has a cross-sectional area of about $1.6 \times 10^{-4}$ inch$^2$ or less and a predetermined length between 4.5 and 100 inches according to a disclosed preferred form of the invention. The length of the elongated passage through which the fluid is flowed is changed to change the flow rate of fluid by selectively bypassing the fluid around a portion or portions of the elongated passage through a relatively large cross-sectional area bypass passage. In the disclosed preferred embodiment of the invention the point at which the fluid is supplied to the elongated passage is varied to change the length of the elongated passage to which the fluid is flowed and thereby change the flow rate of fluid.

According to the disclosed, preferred form of the invention the elongated passage extends in a spiral shape. The number of turns of the spiral shaped passage through which the fluid is flowed is changed to change the flow rate.

The step of providing an elongated passage having a small cross-sectional area according to the method of the invention includes forming a first elongated groove with a small cross-sectional area in a surface of a first member and overlying the groove with a surface of a second member. An inlet and an outlet for communicating the fluid to and from the elongated passage are also formed in at least one of the first and second members. A second groove of a substantially larger cross-sectional area than the elongated passage is formed in the surface of the second member. The second groove is configured such that it can be selectively placed in communication with both an intermediate portion of the first groove and one of the inlet and outlet by selecting the relative position of the first and second members thereby effectively bypassing a portion of the elongated passage and changing the length of the elongated passage through which the fluid is flowed for accomplishing the step of changing the flow rate.

The apparatus of the invention for controlling the flow rate of a fluid comprises means defining an elongated passage having a small cross-sectional area through which a fluid can be flowed, and means for changing the flow rate of a fluid flowing through the elongated passage. The means for changing the flow rate includes means for changing the length of the elongated passage through which the fluid is flowed to thereby change the flow rate of the fluid through the passage. The means for changing the length of the elongated passage through which the fluid is flowed includes means for bypassing the fluid around a predetermined portion or portions of the elongated passage to thereby increase the flow rate of the fluid through the elongated passage. For example, means are provided for changing the point at which the fluid is supplied to the elongated passage. Where the elongated passage is spiral shaped, the number of turns of the spiral shaped passage through which the fluid is flowed is changed to change the flow rate.

Further, according to the apparatus the means defining an elongated passage having a small cross-sectional area includes a first member having a first elongated groove with a small cross-sectional area formed in a surface thereof and a second member having a surface overlying the groove. An inlet and an outlet for communicating the fluid to and from the elongated passage are formed in at least one of the first and second members. The means for changing the length of the elongated passage through which the fluid is flowed to thereby change the flow rate of the fluid through the passage comprises a second groove formed in the surface of the second member. The second groove has a substantially larger cross-sectional area than the elongated passage and acts as a bypass passage to bypass a portion or portions of the elongated passage having a small cross-sectional area. That is, the second groove is configured such that it can be selectively placed in communication with both an intermediate portion of the first groove and one of the inlet and the outlet by selecting the relative position of the first and second members thereby effectively bypassing a portion of the elongated passage and changing the length of the elongated passage through which the fluid is flowed.

Means are provided for holding the first and second members against one another so that the first groove remains sealed by the surface of the second member to retain fluid therein when pressurized fluid is flowed through the elongated passage. Further, means are provided for effecting relative movement of the first and second members to change the length of the elongated passage through which the fluid is flowed.

These and other objects, features and advantages of the present invention will become more apparent from the following description when taken in connection with the accompanying drawings which show, for purposes of illustration only, two preferred embodiments in accordance with the present invention.

DESCRIPTION OF THE DISCLOSED EMBODIMENTS

Figure 1:
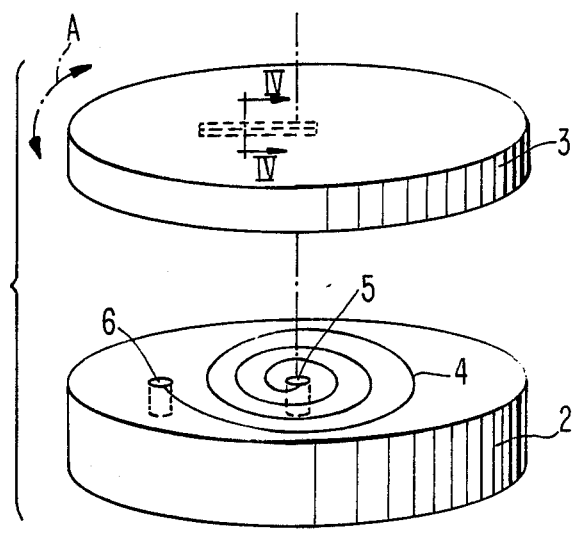
FIG. 1 is a perspective view from the side and slightly above an apparatus for controlling the flow rate of a fluid according to a preferred embodiment of the invention and wherein the first and second members of the apparatus are shown in spaced relationship.
Figure 3:
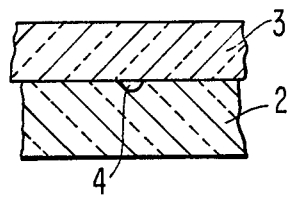
FIG. 3 is a cross-sectional view of a portion of the spiral groove formed in the first member taken along the line III—III of FIG. 2 and illustrating the second member of the apparatus in contact with the grooved surface of the first member to form an elongated passage having a small cross-sectional area through which a fluid can be flowed.
Figure 2:
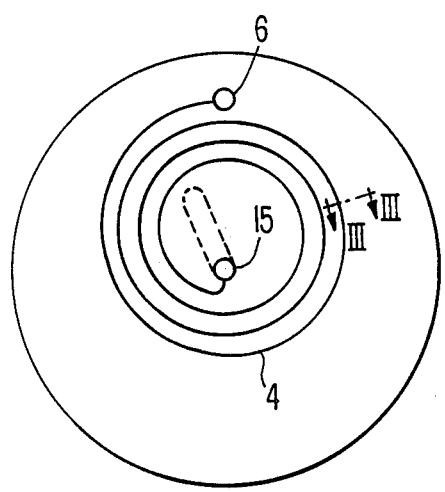
FIG. 2 is a top plan view of the first, lower member of the apparatus of FIG. 1 and wherein the position of the bypass groove formed in the second member is shown in dashed lines.
Figure 4:
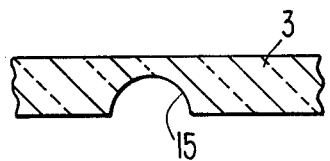
FIG. 4 is a cross-sectional drawing through a portion of the second, upper member of the apparatus in FIG. 1 taken along the line IV—IV and illustrating the cross-sectional shape of the bypass groove in the second member.

Referring now to the drawings, an apparatus 1 according to the invention for controlling the flow rate of a fluid is seen to comprise a first member 2 and a second member 3. The first member 2 is formed with a spiral shaped elongated groove 4 in its upper surface as shown in FIGS. 1-3. The groove 4 is semicircular in cross-section, see FIG. 3, with a radius of curvature which is preferably 0.004–0.010 inch. The length of the spiral shaped groove 4 is preferably within the range of 4.5 to 100 inches. The upper surface of the first member 2 in which the groove 4 is formed in an optically flat surface. The first member 2 is in the form of a circular disc. The radially innermost end of the spiral groove 4 is connected to a relatively large diameter inlet hole 5 formed through the center of the disc for supplying fluid to the elongated passage formed by the groove 4 and the overlying optically flat surface of the second member 3 as discussed more fully hereinafter. The radially outermost end of the spiral groove 4 is connected to a relatively large diameter outlet hole 6 formed through the disc as shown in FIGS. 1, 2 and 5.

The second member 3 is also in the form of a circular disc of the same diameter as the first member 2. The face of the second member 3 adjacent groove 4 is also optically flat, so that the members 2 and 3 can be pressed together to form a sealed, spiral shaped elongated passage having a small cross-sectional area along the length of the elongated groove 4 extending from the inlet hole 5 to the outlet hole 6 of the apparatus. The first and second members 2 and 3 may be formed of fused quartz, for example, although other materials such as sapphire, ceramic, silicon carbide, glass, metal or metal alloy, plastic or combinations thereof may be used. In order to retain fluid within the elongated passage formed along the groove 4, provision is made for biasing the first and second members 2 and 3 toward one another. The total load urging the two opposed operative surfaces of the members 2 and 3 toward one another must be in excess of the fluid pressure tending to separate the two members as discussed more fully below.

Figure 5:
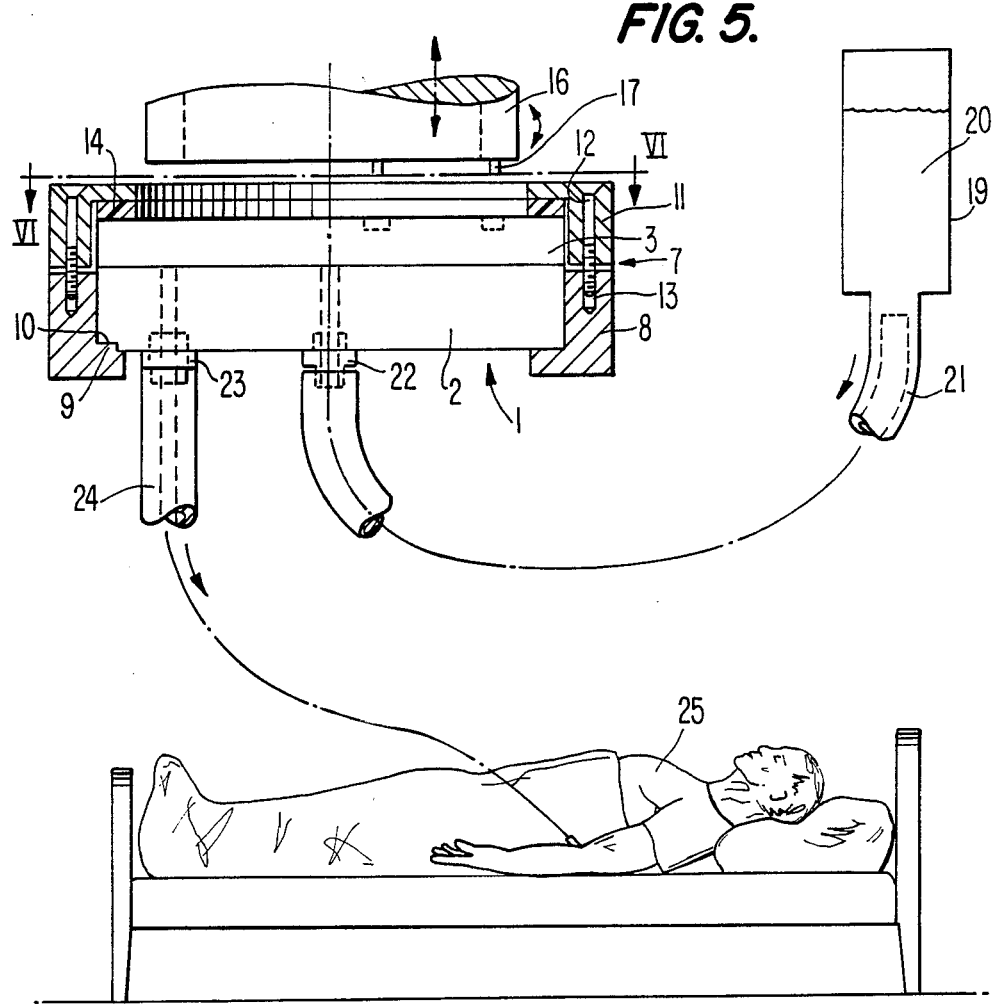
FIG. 5 is a side elevational view, partially in cross-section, of the apparatus of FIG. 1 shown in its assembled condition within a casing for urging the first and second members toward one another with a portion of a tool for adjusting the flow rate being shown above the apparatus and with the apparatus depicted in use for controlling the flow rate of intravenous fluid to a patient.
Figure 6:
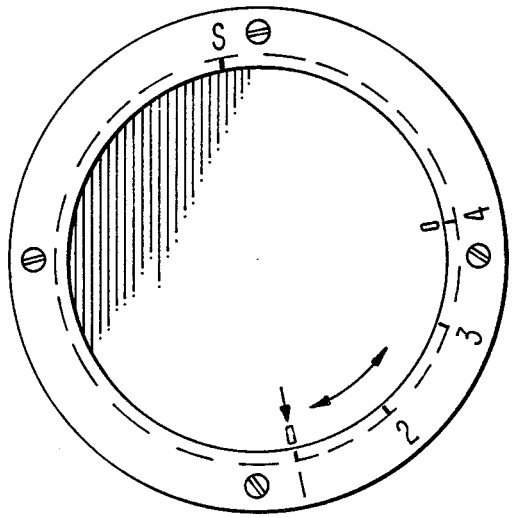
FIG. 6 is a top view of the apparatus shown in FIG. 5 taken along the line VI—VI and illustrating two small slots provided in the top of the second member for receiving projections of the adjusting tool as shown in FIG. 5.

A clamping assembly 7 for urging the first and second members 2 and 3 toward one another is shown in FIGS. 5 and 6. The assembly 7 comprises a lower ring 8 which receives the first member 2 for non-rotatably supporting the same. A projection 9 is formed in one portion of the ring 8 for reception in a complementarily shaped recess 10 formed in the radially outer lower surface of the member 2 as depicted in cross-section in FIG. 5. An upper ring 11 is mounted on the lower ring 8 by means of threaded fasteners 12 extending downwardly from the upper surface of the ring 11 into cooperating threaded bores 13 in the lower ring 8. A resilient washer 14 is positioned between the upper surface of the second member 3 and an inwardly extending flange of the ring 11 for applying a uniform pressure about the second member 3 to urge it into contact with the first member 2. The washer 14 may be formed of a Silastic silicon rubber having a thickness of 0.100 inch and a Shore A hardness of 40. The amount of compression of the elastomeric washer 14 can be adjusted by means of the threaded fasteners 12.

The optically flat lower surface of the second member 3 is formed with a straight groove 15 having a relatively large cross-sectional area as compared with the spiral groove 4. For example, the groove 15 can have a radius of curvature of 0.045 inch. The circular inlet and outlet holes 5 and 6 can have the same radius. The radially inner end of the groove 15 is located at the center of the disc 3 over the inlet hole 5 in member 2 and extends radially outward therefrom. The length of the groove 15 and the asymmetric position of the spiral groove 4 in the member 2 are such that the groove 15 can be positioned wholly within the inner spiral of the groove 4 with the members 2 and 3 in a first predetermined relative position with respect to one another, see FIG. 2. However, rotation of the second member 3 relative to the first member 2, see arrow A in FIG. 1, causes the groove 15 to progressively overlap each of the turns of the spiral groove 4. Since the cross-sectional area of the groove 15 and the inlet hole 5 communicating with the groove 15 are both relatively large as compared with the cross-sectional area of the elongated passage through spiral groove 4, the groove 15 acts to bypass a portion or portions of the spiral passage to thereby increase the rate of flow of the fluid by reducing the length of the elongated passage through which the fluid is flowed. Thus, for a given pressure difference between the inlet and outlet fluid pressures and a given fluid viscosity, the flow rate of the fluid can be incrementally increased from that obtained by flowing the fluid completely through the elongated passage from the inlet hole 5 to the outlet hole 6 by rotating the second member 3 relative to the first member 2 so that the bypass groove 15 extends over and communicates with one or more of the turns of the spiral groove 4 thereby reducing the length of the small cross-sectional area passage through which the fluid is flowed.

Relative rotation of the first and second members 2 and 3 can be accomplished using the tube 16 illustrated in FIG. 5. The lower end of the tube 16 is provided with a pair of projections 17 extending outwardly therefrom. A pair of recesses 18 are formed in the top of the second member 3 for receiving the projections 17. When the projections are inserted into the recesses 18, rotation of the tube 16 causes the second member 3 to rotate relative to the first member 2, which is held in a stationary position by means of the cooperating projection 9 of the lower ring 8 and recess 10 in the first member 2. Suitable indicia can be provided about the top surface of the upper ring 11 for appropriately setting the position of the second member 3 and thus the bypass groove 15 with respect to the spiral groove 4. For example, the positions 1–5 shown in FIG. 6 could correspond, respectively, to the use of an elongated passage having the length corresponding to the full length of the spiral groove 4, the inner turn of the spiral groove 4 being overlapped by the bypass groove 15, the inner two turns of the spiral groove 4 being overlapped and therefore bypassed by the bypass groove 15, etc. For a known fluid and fluid pressure difference, the indicia 1–5 would therefore correspond to known, incrementally increased flow rates which could readily be selected by the operator by merely rotatably adjusting the position of the first member 2 with respect to the second member 3 using the adjusting tube 16.

The apparatus of the invention can be used, for example, to control the flow rate of a liquid during intravenous infusion. A receptacle 19 shown in FIG. 5 contains a liquid 20 such as a saline solution of 0.09% NaCl in water or 0.05% dextrose in water for intravenous infusion. The liquid 20 is led from the receptacle 19 by means of a tube 21 to the inlet hole 5 of the apparatus 1 of the invention. An inlet fitting 22 is shown attached to the lower surface of the first member 2 for receiving the tube 20. Likewise, an outlet fitting 23 is attached to the first member at the outlet hole 6 as by a threaded connection, for example, for receiving a tube 24 leading to a patient 25. The inlet pressure of the liquid 20 at the inlet hole 5 can be 2½ psi above atmospheric, for example, with the outlet pressure at the outlet hole 6 of the apparatus being 1 psi above atmospheric pressure. In such a case, the mean psi experienced by the apparatus 1 is 1¾ psi. Therefore, the preload on the first and second members by means of the clamping assembly 7 with elastomeric washer 14 must be in excess of 1¾ × the total fluid channel area between the two members. The latter can be calculated by multiplying the length of the groove 4 times the width thereof and adding thereto the cross-sectional area of the inlet hole 5, outlet hole 6 and bypass groove 15. In this example, the apparatus 1 could be used to change the rate of infusion of the liquid 20 to the patient 25 in increments over the range of 4–12 liters per hour, in one hour increments, for example, by changing the relative position of the members 2 and 3 as discussed above. Since the inlet fitting 22 and outlet fitting 23 remain connected to the spiral groove 4 during flow rate adjustment and the bypass groove 15 is always in communication with the fluid passage at least at one end thereof, with the apparatus of the invention, fluid continues to flow through the apparatus even during adjustment of the flow rate, that is, there is no interruption or discontinuation of the flow during adjustment of the flow rate.

While the sealing between the opposed optically flat faces of the first and second members 2 and 3 is accomplished by merely urging the two members toward one another in the disclosed embodiment, according to a further feature of the invention, if desired, a thin film of polyvinyl alcohol (PVA) or kapton (a polyimide) of up to 0.030 inch thickness could be provided between the first and second members 2 to assist in sealing about the elongated passage, bypass groove and the inlet and outlet holes. The flexible PVA or kapton layer should be sufficiently resilient so as to yield and expand into the bypass groove 15 when the groove is moved into overlaping relationship with a turn or turns of the spiral groove 4 to permit the bypass groove to conduct fluid directly from the inlet to the outermost overlapped turn thereof and therefore effectively bypass the intermediate portion of the elongated passage.

Figure 7:
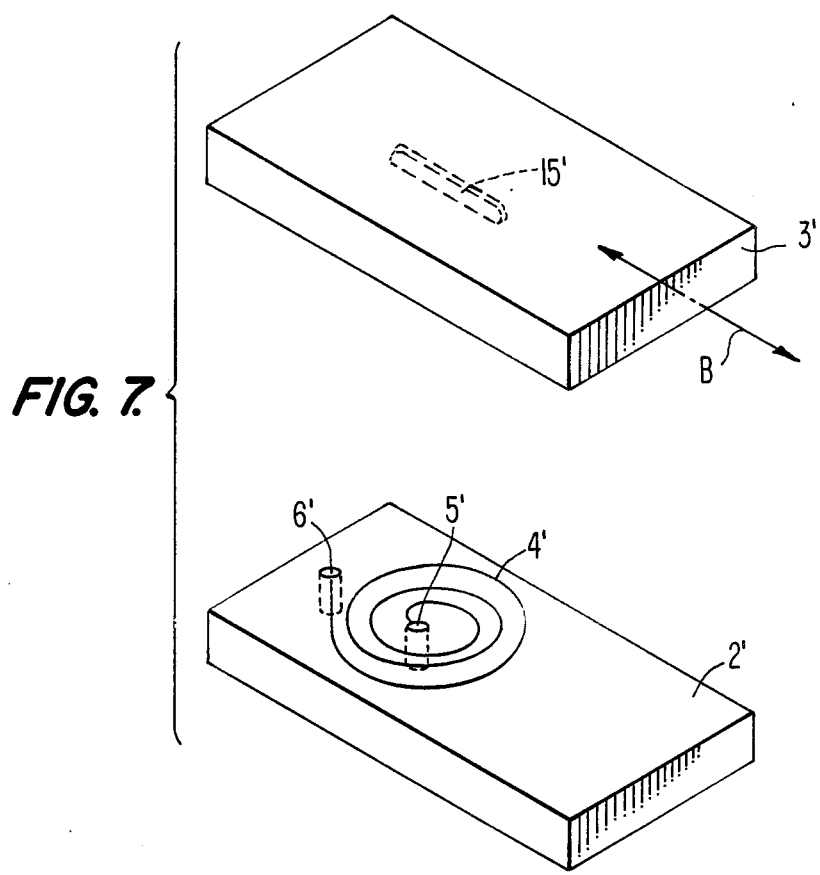
FIG. 7 is a perspective view from the side and slightly above of an apparatus according to a second embodiment of the invention wherein the first and second members are shown in spaced relationship for illustration purposes.
Figure 8:
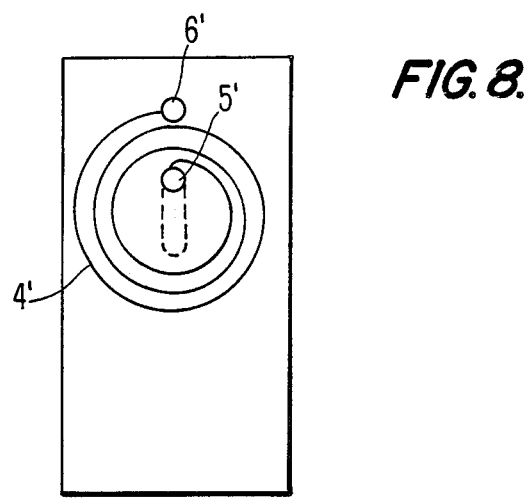
FIG. 8 is a top plan view of the first, lower member of the apparatus of FIG. 7 with the position of the bypass groove of the overlying second member being shown in dashed lines thereon.

In the form of the invention illustrated in FIGS. 7 and 8 of the drawings, the first and second members 2' and 3' are rectangular in shape with relative movement of the two members being effected by sliding the members relative to one another in a linear fashion along the length of the rectangular members as shown by the arrow B in FIG. 7. The operation and structure of the apparatus of this embodiment are otherwise the same as those described above with respect to the embodiment of FIGS. 1–6.

The first and second members of the apparatus of the invention as referred to above can be formed of any hard, stable material that can be made very flat and which is not readily subjected to cold flow. The upper and lower members can be of different materials selected primarily for their low coefficient of friction, so as to facilitate the relative movement of the members in the manner previously discussed.

While I have shown and described only two embodiments in accordance with the present invention, it is understood that the same is not limited thereto, but is susceptible to numerous changes and modifications as known to those skilled in the art. For example, the elongated passage need not be in the form of a spiral, but could have other shapes which, in cooperation with the shape of the bypass groove, permit the overlapping or bypassing of portions of the elongated passage thereby changing the effective length of the elongated passage and the resulting flow rate of the fluid passing through the apparatus. Also, the apparatus and method of the invention are not limited to use with liquids, but have applicability for controlling the flow of gas as in gas chromatography processes, for example. Other possible applications of the invention include metering drugs into diluents for the preparation of different fluid drug concentrations, metering colorings and dies into foodstuffs, and metering catalysts and resins in the preparation of adhesives. The apparatus and method also have applicability for implantable and external drug infusion devices for human and animal use. Therefore, I do not wish to be limited to the details shown and described herein, but intend to cover all such changes and modifications as are encompassed by the scope of the appended claims.

I claim:

1. A method for controlling the flow rate of a liquid to a patient comprising the steps of providing a receptacle containing a liquid to be administered to a patient and fluid passage means for conveying said liquid from said receptacle to said patient, said fluid passage means including an elongated passage having a small cross-sectional area, supplying liquid from said receptacle to said elongated passage to flow said liquid through a first predetermined length of said elongated passage at a first flow rate, and stepwise incrementally changing the flow rate of liquid in said passage from said first flow rate to a second flow rate without interrupting the flow of said liquid in said passage by incrementally changing the length of said elongated passage through which said liquid is flowed from said first predetermined length to a second predetermined length, wherein said step of providing an elongated passage having a small cross-sectional area includes forming a first elongated groove with a small cross-sectional area in a surface of a first member and overlying said groove with a surface of a second member, and providing an inlet and an outlet for communicating said liquid to and from said elongated passage, and wherein a second groove of a substantially larger cross-sectional area than said elongated passage is formed in said surface of said second member, said second groove being configured such that it can be selectively and progressively placed in simultaneous communication with each of a plurality of spaced intermediate portions of said first groove and one of said inlet and said outlet by selecting the relative position of said first and second members, thereby effectively and progressively by-passing respective portions of said elongated passage and stepwise incrementally changing the length of said elongated passage through which said liquid is flowed for accomplishing said step of changing the flow rate without interrupting the liquid flow through said passage to said patient.

2. A method according to claim 1, wherein said elongated passage has a cross-sectional area of about $1.6 \times 10^{-4}$ inch$^2$ or less.

3. A method according to claim 1, wherein said elongated passage has a length between 4.5 and 100 inches.

4. A method according to claim 1, wherein said step of changing the flow rate by changing the length of said elongated passage through which said liquid is flowed comprises changing the point at which the liquid is supplied to said elongated passage.

5. A method according to claim 1, wherein said elongated passage extends in a spiral shape.

6. A method according to claim 5, wherein said step incrementally of changing the flow rate by changing the length of said elongated passage through which said fluid is flowed comprises changing the number of turns of said spiral shaped passage through which said fluid is flowed.

7. An apparatus for controlling the flow rate of a liquid to a patient comprising means defining an elongated passage having a small cross-sectional area through which a liquid can be flowed, and means for changing the flow rate of a liquid flowing through said elongated passage without interrupting the liquid flow in said elongated passage, said means for changing the flow rate including means for stepwise incrementally changing the length of said elongated passage through which said liquid is flowed, thereby incrementally changing the flow rate of said liquid through said passage, wherein said means defining an elongated passage having a small cross-sectional area includes a first member having a first elongated groove with a small cross-sectional area formed in a surface thereof and a second member having a surface overlying said groove to form said elongated passage, wherein an inlet and an outlet for communicating said liquid to and from said elongated passage are formed in at least one of said first and second members, and wherein said means for incrementally changing the length of said elongated passage through which said liquid is flowed to thereby change the flow rate of said liquid through said passage comprises a second groove formed in said surface of said second member and having a substantially larger cross-sectional area than said elongated passage, said second groove being configured such that it can be selectively progressively placed in simultaneous communication with each of a plurality of spaced intermediate portions of said first groove and one of said inlet and said outlet by selecting the relative position of said first and second members, thereby effectively and progressively by-passing respective portions of said elongated passage and stepwise incrementally changing the length of said elongated passage through which said liquid is flowed without interrupting the liquid flow through said passage to said patient.

8. An apparatus according to claim 7, wherein said elongated passage has a cross-sectional area on the order of $1.6 \times 10^4$ inch$^2$ or less.

9. An apparatus according to claim 7, wherein the length of said elongated passages between 4.5 and 100 inches.

10. An apparatus according to claim 7, wherein said means for incrementally changing the length of said elongated passage through which said liquid is flowed includes means for changing the point at which said liquid is supplied to said elongated passage.

11. An apparatus according to claim 7, wherein said elongated passage extends in a spiral shape.

12. An apparatus according to claim 11, wherein said means for incrementally changing the length of said elongated passage through which said liquid is flowed changes the number of turns of said spiral shaped passage through which said liquid is flowed.

13. An apparatus according to claim 7, wherein means are provided for effecting relative movement of said first and second members to change the length of said elongated passage through which said liquid is flowed.

14. An apparatus according to claim 7, wherein means are provided for urging said first and second members toward one another to seal said elongated passage when pressurized liquid is flowed through said elongated passage.

* * * * *